(12) United States Patent
Kollmer

(10) Patent No.: US 9,907,597 B2
(45) Date of Patent: Mar. 6, 2018

(54) BONE COMPRESSION SYSTEM AND ASSOCIATED METHODS

(71) Applicant: Charles E. Kollmer, Edgewater, FL (US)

(72) Inventor: Charles E. Kollmer, Edgewater, FL (US)

(73) Assignee: Charles E. Kollmer, Edgewater, FL (US)

( * ) Notice: Subject to any disclaimer, the term of this patent is extended or adjusted under 35 U.S.C. 154(b) by 0 days.

(21) Appl. No.: 15/002,017

(22) Filed: Jan. 20, 2016

(65) Prior Publication Data
US 2016/0135861 A1    May 19, 2016

Related U.S. Application Data

(63) Continuation-in-part of application No. 13/057,824, filed as application No. PCT/US2009/052182 on Jul. 30, 2009, now Pat. No. 9,247,963.
(Continued)

(51) Int. Cl.
*A61B 17/58* (2006.01)
*A61B 17/88* (2006.01)
(Continued)

(52) U.S. Cl.
CPC ...... *A61B 17/8866* (2013.01); *A61B 17/1767* (2013.01); *A61B 17/683* (2013.01);
(Continued)

(58) Field of Classification Search
CPC . A61B 17/683; A61B 17/68; A61B 2017/681; A61B 17/1767; A61B 17/842; A61B 17/864; A61B 17/8665
(Continued)

(56) References Cited

U.S. PATENT DOCUMENTS 2,485,531 A    10/1949   Dzuz et al.
2,489,870 A  * 11/1949   Dzus .................. A61B 17/683
                                                            411/339
(Continued)

FOREIGN PATENT DOCUMENTS

DE    202007017159 U1    5/2008
EP         0792621 A1    3/1997

OTHER PUBLICATIONS

PCT/US2009/052182, PCT International Search Report dated Oct. 29, 2009, from which the instant application is based. 4 Pages.
(Continued)

*Primary Examiner* — Tatiana Nobrega
*Assistant Examiner* — Jessica Weiss
(74) *Attorney, Agent, or Firm* — Mark Malek; Paul Ditmyer; Widerman Malek, PL

(57) ABSTRACT

Systems and associated methods for repairing first and second bone fragments include a bone compression device characterized by an elongated fastener and an anchor. The fastener includes an externally-threaded shank, an enlarged head, and a bore extending through both. The anchor includes an internally-threaded bore configured to receive the threaded shank of the fastener at a first end of the anchor, and an enlarged shoulder at a second end. The fastener inserts fittedly into a first bore formed in the first and second bone fragments, with the head engaging a rim of the first bore. The anchor inserts fittedly into a second bore formed in the second bone fragment, the anchor shoulder engaging a rim of the second bore. During compression of the bone segments, a small space is maintained between the second end of the anchor and an intersection of the first bore and the second bore.

9 Claims, 16 Drawing Sheets

Related U.S. Application Data

(60) Provisional application No. 61/088,040, filed on Aug. 12, 2008.

(51) Int. Cl.

| *A61B 17/86* | (2006.01) |
| *A61B 17/68* | (2006.01) |
| *A61B 17/17* | (2006.01) |
| *A61B 50/20* | (2016.01) |
| *A61B 50/22* | (2016.01) |
| *A61B 50/33* | (2016.01) |
| *A61B 50/34* | (2016.01) |
| *A61B 17/16* | (2006.01) |
| *A61B 17/82* | (2006.01) |
| *A61B 90/00* | (2016.01) |

(52) U.S. Cl.
CPC ........ *A61B 17/864* (2013.01); *A61B 17/8665* (2013.01); *A61B 17/8685* (2013.01); *A61B 17/8875* (2013.01); *A61B 50/20* (2016.02); *A61B 50/22* (2016.02); *A61B 50/33* (2016.02); *A61B 50/34* (2016.02); *A61B 17/1615* (2013.01); *A61B 17/82* (2013.01); *A61B 17/8695* (2013.01); *A61B 2017/681* (2013.01); *A61B 2090/062* (2016.02)

(58) Field of Classification Search
USPC ........................ 606/300–309, 322–324, 329; 623/20.18–20.2; 411/5, 40, 42, 55, 338
See application file for complete search history.

(56) References Cited

U.S. PATENT DOCUMENTS

| 3,723,061 | A | * | 3/1973 | Stahl ........................ A61L 2/26 206/370 |
| 3,917,299 | A | | 11/1975 | Anderson |
| 5,193,672 | A | * | 3/1993 | Long ........................ A61L 2/26 206/370 |
| 5,203,770 | A | | 4/1993 | Wigness et al. |
| 5,217,462 | A | * | 6/1993 | Asnis ..................... A61B 17/74 606/105 |
| 5,498,265 | A | * | 3/1996 | Asnis ..................... A61B 17/74 606/315 |
| 5,827,285 | A | | 10/1998 | Bramlet |
| 5,849,004 | A | | 12/1998 | Bramlet |
| 5,976,139 | A | | 11/1999 | Bramlet |
| 5,984,970 | A | | 11/1999 | Bramlet |
| 6,183,474 | B1 | | 2/2001 | Bramlet et al. |
| 6,302,887 | B1 | * | 10/2001 | Spranza ............... A61B 17/683 411/338 |
| 6,355,043 | B1 | | 3/2002 | Adam |
| 6,426,041 | B1 | * | 7/2002 | Smith ...................... A61L 2/26 206/223 |
| 6,443,954 | B1 | | 9/2002 | Bramlet et al. |
| 6,447,546 | B1 | | 9/2002 | Bramlet et al. |
| 6,488,684 | B2 | | 12/2002 | Bramlet et al. |
| 6,632,224 | B2 | | 10/2003 | Cachia et al. |
| 6,648,889 | B2 | | 11/2003 | Bramlet et al. |
| 6,695,844 | B2 | * | 2/2004 | Bramlet ............. A61B 17/1659 606/282 |
| 7,204,838 | B2 | | 4/2007 | Jackson |
| 7,235,079 | B2 | * | 6/2007 | Jensen ............... A61B 17/8685 606/151 |
| 7,749,276 | B2 | | 7/2010 | Fitz |
| 7,837,717 | B2 | | 11/2010 | Deffenbaugh et al. |
| 2002/0198527 | A1 | | 12/2002 | Muckter |
| 2004/0210227 | A1 | * | 10/2004 | Trail .................... A61B 17/863 606/916 |
| 2006/0015105 | A1 | * | 1/2006 | Warren .................. A61B 17/68 606/301 |
| 2007/0225819 | A1 | | 9/2007 | Eva |
| 2009/0228049 | A1 | | 9/2009 | Park |

OTHER PUBLICATIONS

PCT/US2009/052182, PCT Written Opinion dated Oct. 29, 2009, from which the instant application is based. 7 Pages.
U.S. Appl. No. 13/057,824, USPTO Non-Final Office Action dated Nov. 30, 2012.
U.S. Appl. No. 13/057,824, Applicant Amendment/Request for Reconsideration After Non-Final Rejection dated May 30, 2013.
U.S. Appl. No. 13/057,824, USPTO Final Office Action dated Sep. 25, 2013.
U.S. Appl. No. 13/057,824, Applicant Response After Final Rejection dated Dec. 20, 2013.
U.S. Appl. No. 13/057,824, USPTO Advisory Action Before Filing of an Appeal Brief dated Jan. 9, 2014.
U.S. Appl. No. 13/057,824, Applicant Request for Continued Examination and Amendment dated Feb. 11, 2014.
U.S. Appl. No. 13/057,824, USPTO Non-Final Office Action dated Jan. 16, 2015.
U.S. Appl. No. 13/057,824, Applicant Amendment/Request for Reconsideration After Non-Final Office Rejection dated Apr. 16, 2015.
U.S. Appl. No. 13/057,824, USPTO Final Office Action dated Jun. 25, 2015.
U.S. Appl. No. 13/057,824, Applicant Certification and Request for Consideration Under the After Final Consideration Pilot Program 2.0 dated Sep. 3, 2015.
U.S. Appl. No. 13/057,824, Applicant Response After Final Rejection dated Sep. 3, 2015.
PCT International Search Report for related application PCT/US2017/012256 dated Apr. 7, 2017; 6 pages.
PCT Written Opinion for related application PCT/US2017/012256 dated Apr. 7, 2017; 7 pages.

\* cited by examiner

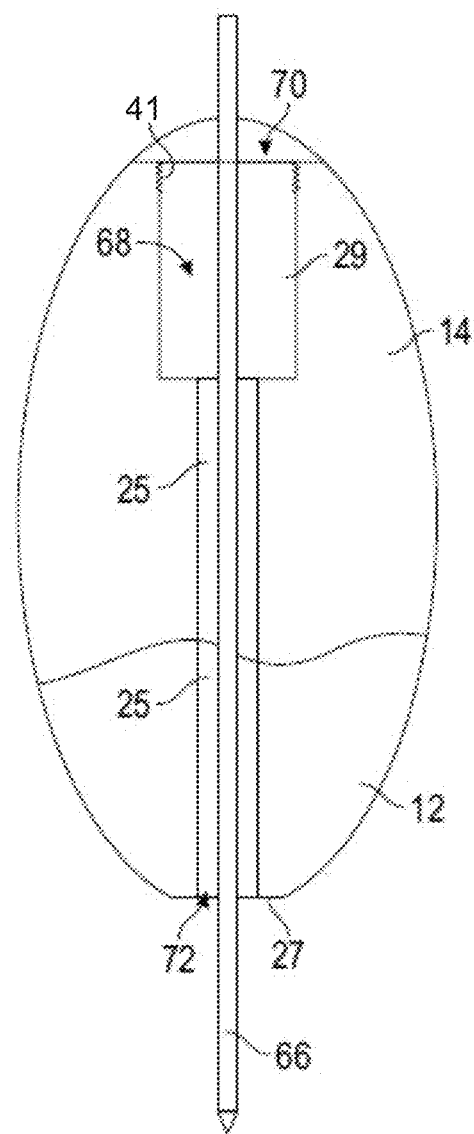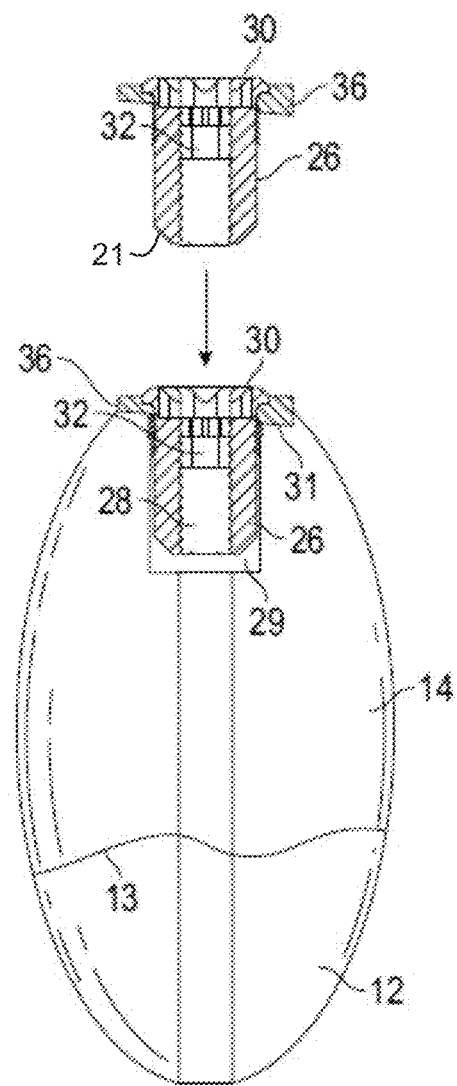
FIG. 13
FIG. 14

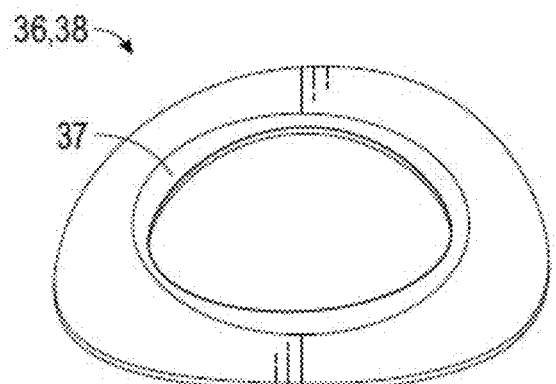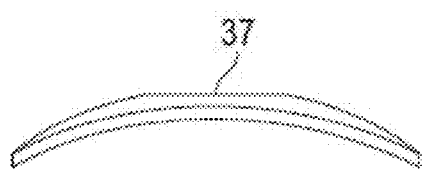
FIG. 18A              FIG. 18B
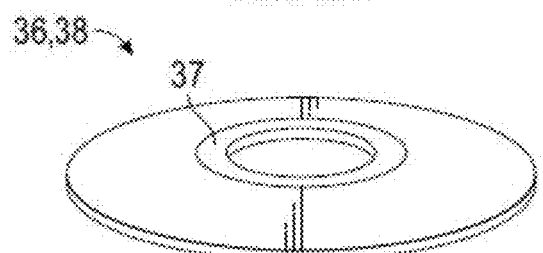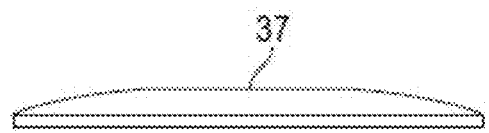
FIG. 19A              FIG. 19B
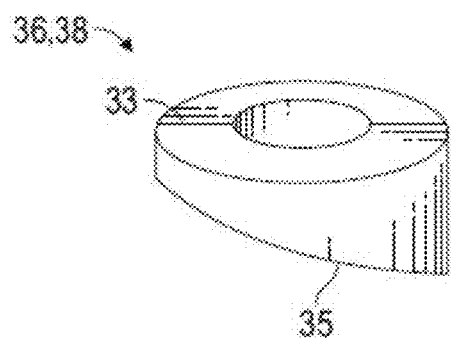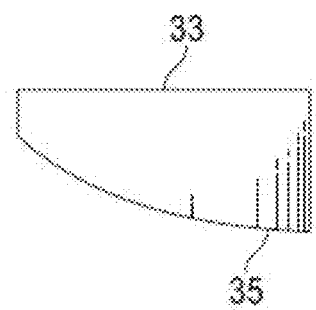
FIG. 20A              FIG. 20B
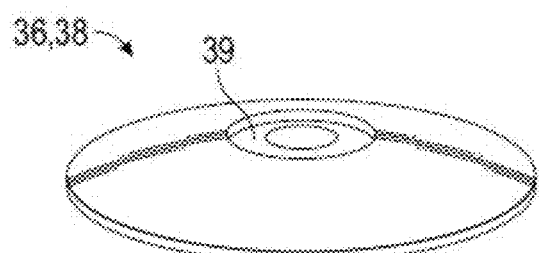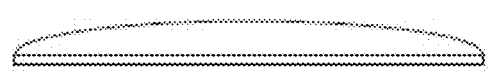
FIG. 21A              FIG. 21B

BONE COMPRESSION SYSTEM AND ASSOCIATED METHODS

RELATED APPLICATIONS

This application is a continuation-in-part and claims the benefit under 35 U.S.C. § 120 of U.S. patent application Ser. No. 13/057,824 filed on Feb. 7, 2011 as the National Stage Entry of International Application No. PCT/US09/52182, and titled Bone Compression Device And Methods, and which, in turn, claims the benefit under 35 U.S.C. § 119(e) of U.S. Provisional Patent Application Ser. No. 61/088,040 filed on Aug. 12, 2008 and titled Bone Compression Device And Methods, the entire contents of each of which are incorporated herein by reference.

FIELD OF THE INVENTION

The present invention relates to devices and methods for fixing together two or more bone fragments following a fracture. More particularly, embodiments of the present invention relate to devices and methods for compressing bone fragments together along fracture surfaces.

BACKGROUND

Fractured bone fragments typically must be held together for extended time periods to promote healing. Adjoining fragments of a severed or fractured bone are typically clamped together or attached to one another through the use of pins or screws driven through the separated portions of bone, or are fixed in place using a splint.

In general, bones are formed of a relatively soft, spongy cancellous material surrounded by a much harder cortex. Cancellous bone yields under relatively low loading, while the much denser cortical bone supports much higher loading. In some cases, fixation devices are used to secure the broken parts together through direct fixation in the bone. However, due to the soft nature of the cancellous material, fixation devices may tend to disassemble as screws and nails loosen from the bone material over time.

In some cases, compression screws are used to compress together bone fragments. Given relatively high loading, compression screws can tend to back out once implanted, thus leading to unwanted discomfort and potentially recurring surgery. While a number of techniques and devices have been developed for fixing bones together for healing, these and other issues remain. Thus, an improved bone compression device with strong purchase and no backing out is desired.

This background information is provided to reveal information believed by the applicant to be of possible relevance to the present invention. No admission is necessarily intended, nor should be construed, that any of the preceding information constitutes prior art against the present invention.

SUMMARY OF THE INVENTION

With the above in mind, embodiments of the present invention are related to systems and methods that employ a bone compression device for compressing together first and second bone fragments is provided. The compression device generally includes an elongated fastener with an externally-threaded portion, an anchor with an internally-threaded bore for threadedly receiving the externally-threaded portion of the fastener and a lock for locking together the fastener and the anchor against relative rotation. In some embodiments, the bone compression device may include a fastener with a threaded shank portion that is threadingly received within the anchor when the fastener and anchor are operably positioned to compress the first and second bone fragments to a desired degree. The lock may be in the form of an externally-threaded locking screw threadedly receivable within the anchor, coaxial with the fastener portion. In an operative position, the locking screw may be advanced within the anchor bore to lock the position of the fastener portion within the anchor bore.

In some embodiments the fastener is insertable through a first bore formed in the first and second bone fragments such that the fastener shank portion extends through the first bone fragment into the second bone fragment. The fastener may include an enlarged head portion engaging a rim of the first bore in the first bone fragment. The anchor is insertable into a second bore formed in the second fragment, the second bore being of greater diameter than the first bore, coaxial with the first bore, and forming a counterbore floor at an intersection of the first bore and the second bore. An anchor shoulder engages a rim of the second bore such that in an operative position the anchor shoulder and the fastener head portion compress the first and second bone fragments together, while maintaining a small space between the counterbore floor of the second bore and the first end of the anchor. The small space may be a distance ranging from three (3) millimeters down to a minimum distance required to prevent contact of the first end of the anchor with the counterbore floor of the second bore based on a bending moment of the second bone fragment.

Some exemplary anchors include an internally extending lip about the second end of the anchor, which provides access to an externally-threaded locking screw while preventing the locking screw from being removed through the second end of the anchor. The lip may extend about substantially the entire circumference of the anchor's internally-threaded bore at the second end of the anchor, or may be provided as one or more segments protruding into the bore of the anchor. Other exemplary anchors include an externally-threaded portion configured to be received by a threaded-inner surface portion of the second bore in the second bone fragment.

In certain embodiments, the bone compression device may include an exterior washer about the fastener and/or anchor for engaging the bore rims and forming part of the fastener head portion and anchor shoulder portions, respectively. In some cases, the washers may include a substantially flat section positioned atop a chamfer-shaped, wedge-shaped, and curve-shaped surface.

According to another aspect of the invention, a method of fixing first and second bone fragments using a bone compression device is provided. In addition to providing a bone compression device according to embodiments of the invention, forming a first bore may be formed in the first bone fragment and at least partially through the second bone fragment. Also, a second bore may be formed in the second bone fragment having a greater diameter than the first bore, positioned coaxial with the first bore, and defining a counterbore floor at an intersection of the first bore and the second bore. In some cases, the counterbore floor of the second bore is squared-off. The first end of the anchor may be inserted into the second bore such that the anchor shoulder is positioned in contact with a rim of the second bore so as to define the small space between the counterbore floor of the second bore and the first end of the anchor. The shank portion of the fastener is inserted through the first bore and into the second bore, and the externally-threaded portion of the fastener shank portion is advanced into the first end of the anchor until the fastener head portion contacts a rim of the first bore. Accordingly, the fastener and anchor operate to adjustably compress the first and second bone fragments together. Further, a lock, such as a locking screw, is coaxially advanced through the anchor towards the fastener to engage the second end of the fastener shank portion and to lock together the fastener and the anchor. In some cases, the locking screw may be inserted into the anchor prior to inserting the anchor into a bore. The locking screw may then be prevented from being removed from the exterior end of the anchor, for example, by a rounded lip protruding inwardly at the exterior end of the anchor.

In some embodiments, the method further includes providing one or more washers positioned about a perimeter of the anchor and/or the fastener. The washers may in some cases be custom-selected by shape and/or size to deliver compressive force about a bone segment with which the washer makes contact. Methods of using a bone compression device may further include forming a countersunk depression in the first bone fragment about the rim of the first bore and/or forming a countersunk depression in the second bone fragment about the rim of the second bore to accommodate the fastener head, the anchor shoulder, and/or one or more washers.

In some embodiments, a method further includes selecting the fastener of the first bone compression device from a plurality of fasteners of different lengths, such that the threaded portion of the fastener shank will be substantially received within the anchor when the fastener and anchor compress the first and second bone fragments to a desired degree.

According to another aspect of the invention, a kit for compressing together first and second bone fragments may include a plurality of elongated fasteners of different lengths, one or more anchors and locks, and a plurality of driving tools for advancing and securing the fasteners, the anchor, and the locks. The kit may further include a plurality of Kirschner wires and a cannulated clamp.

BRIEF DESCRIPTION OF THE DRAWINGS

FIG. 13 is a schematic illustration of the patella of FIG. 11 showing bores formed therein according to an embodiment of the present invention.

FIG. 14 illustrates the insertion of an anchor into a bore formed in the patella of FIG. 13 according to an embodiment of the present invention.

FIG. 18A is a perspective view of a washer according to an embodiment of the present invention.

FIG. 18B is a side view of the washer of FIG. 18A.

FIG. 19A is a perspective view of a washer according to an embodiment of the present invention.

FIG. 19B is a side view of the washer of FIG. 19A.

FIG. 20A is a perspective view of a washer according to an embodiment of the present invention.

FIG. 20B is a side view of the washer of FIG. 20A.

FIG. 21A is a perspective view of a washer according to an embodiment of the present invention.

FIG. 21B is a side view of the washer of FIG. 21A.

DETAILED DESCRIPTION OF THE INVENTION

Figure 1A:
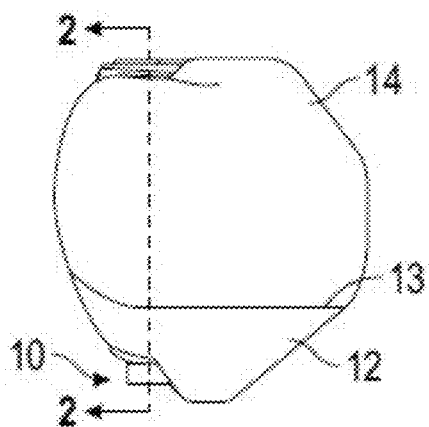
FIG. 1A is a front view of two bone fragments fixed by a bone compression device according to an embodiment of the present invention.

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art realize that the following descriptions of the embodiments of the present invention are illustrative and are not intended to be limiting in any way. Other embodiments of the present invention will readily suggest themselves to such skilled persons having the benefit of this disclosure. Like numbers refer to like elements throughout.

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the claimed invention.

In this detailed description of the present invention, a person skilled in the art should note that directional terms, such as "above," "below," "upper," "lower," and other like terms are used for the convenience of the reader in reference to the drawings. Also, a person skilled in the art should notice this description may contain other terminology to convey position, orientation, and direction without departing from the principles of the present invention.

Furthermore, in this detailed description, a person skilled in the art should note that quantitative qualifying terms such as "generally," "substantially," "mostly," and other terms are used, in general, to mean that the referred to object, characteristic, or quality constitutes a majority of the subject of the reference. The meaning of any of these terms is dependent upon the context within which it is used, and the meaning may be expressly modified.

The following detailed description should be read with reference to the drawings, in which like elements in different drawings are numbered identically. It will be understood that embodiments shown in the drawings and described herein are merely for illustrative purposes and are not intended to limit the invention to any embodiment. On the contrary, it is intended to cover alternatives, modifications, and equivalents as may be included within the scope of the invention as defined by the appended claims.

Embodiments of the present invention, as shown and described by the various figures and accompanying text, provide a bone compression device and methods for compressing bone that are particularly suited for holding together two or more bone fragments, to permit the bone fragments to knit together. According to some embodiments, the bone compression device is particularly suited for fractures of the patella. However, the invention is not restricted to any particular anatomy and may be helpful in fixing a wide variety of bones.

Figure 1B:
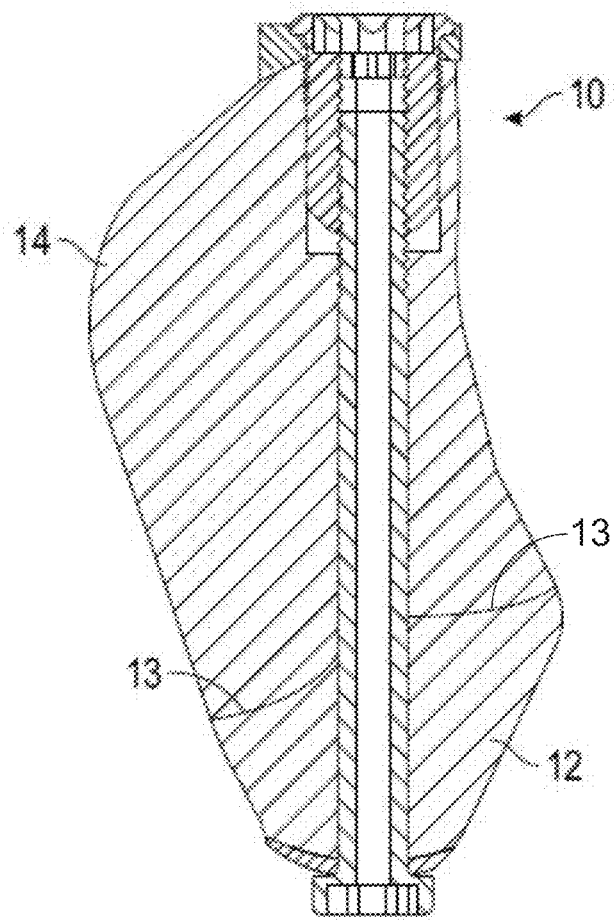
FIG. 1B is a cross-section view of the two bone fragments and bone compression device of FIG. 1A along the section 2-2.

FIGS. 1A and 1B illustrate a bone compression device 10 that may be used to advantageously fix, for purposes of promoting healing, a first bone fragment 12 and a second bone fragment 14 according to an embodiment of the invention. As shown in FIGS. 1A and 1B, for example, and without limitation, the bone compression device 10 may be adapted to compress together the fractured portions of a patella 12, 14 according to this embodiment; that is, to reduce a fracture 13 by compressing the bone fragments 12, 14 together along the fracture line 13.

Figure 2A:
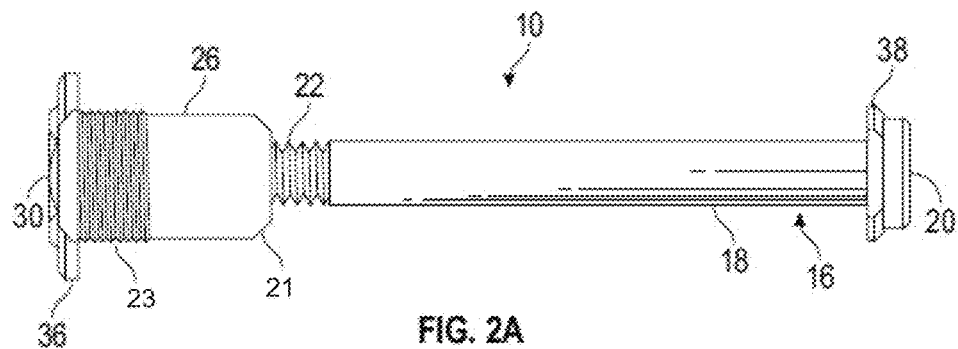
FIG. 2A is a side view of an assembled bone compression device according to an embodiment of the present invention.
Figure 2B:
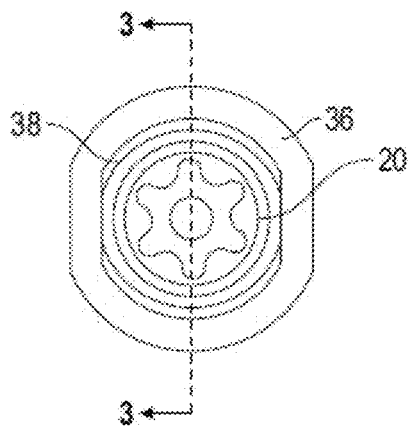
FIG. 2B is an end view of the bone compression device of FIG. 2A taken from the right end of FIG. 2A.
Figure 2C:
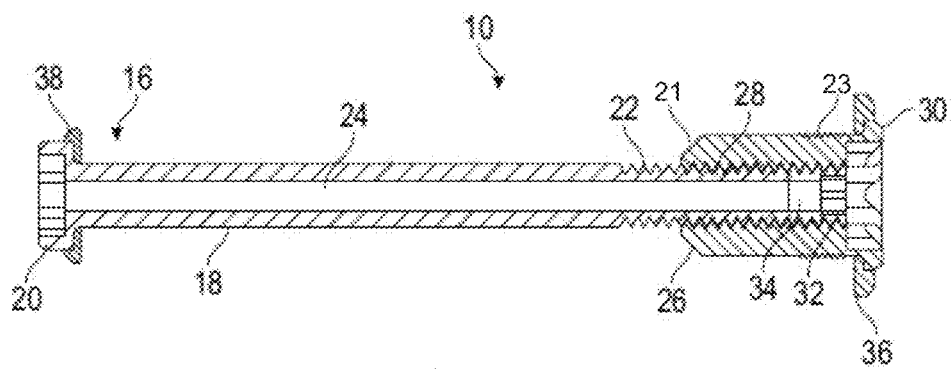
FIG. 2C is a cross-section view of the bone compression device of FIGS. 2A and 2B taken along section 3-3 of FIG. 2B.
Figure 3:
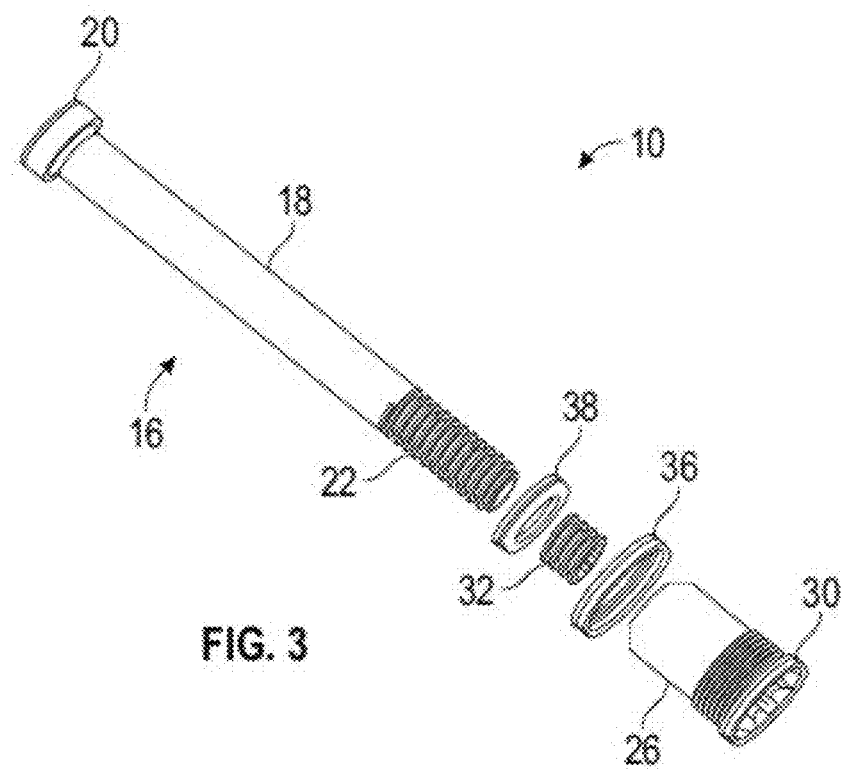
FIG. 3 is an exploded perspective view of the bone compression device of FIG. 2A.
Figure 4A:
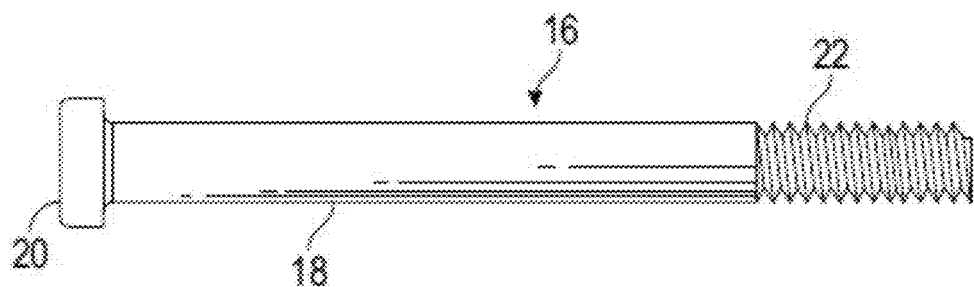
FIG. 4A is a side view of an elongated fastener according to an embodiment of the present invention.
Figure 4B:
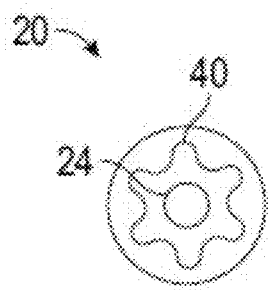
FIG. 4B is an end view of a head of the elongated fastener of FIG. 4A.
Figure 5A:
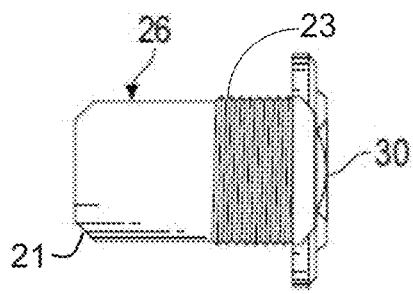
FIG. 5A is a side view of an anchor according to an embodiment of the present invention.
Figure 5B:
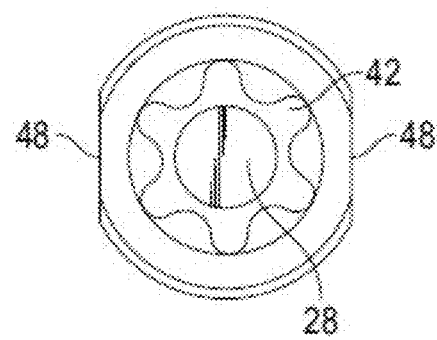
FIG. 5B is an end view of a drive head of the anchor of FIG. 5A.

FIGS. 2A-2C illustrate various views of the assembled bone compression device 10, and FIG. 3 illustrates an exploded view of the bone compression device 10. According to certain embodiments, the bone compression device 10 may include an elongated fastener 16 having a shank portion 18 with an enlarged head portion 20 at one end and an externally-threaded portion 22 at the other end. A bore 24 may extend through the head 20 and shank 18 portions providing access through the fastener 16. For example, and without limitation, the fastener 16 may comprise an exteriorly-threaded 22, cannulated (thinly bored 24) bolt with an enlarged cap 20 at one end. The shank portion 18 of the fastener 16 may be characterized by a diameter between 6.0 and 6.2 millimeters. The bore 24 of the fastener 16 may be characterized by a diameter between 3.0 and 6.0 millimeters.

Continuing to refer to FIGS. 2A-2C, and referring additionally to FIG. 3, the bone compression device 10 may include an anchor 26 that may comprise an internally-threaded bore 28 that may be configured to threadedly receive the externally-threaded shank portion 22 of the fastener 16. The shank portion 22 may be received in a first end of the anchor 26, while a second end of the anchor 26 may include an enlarged shoulder 30. For example, and without limitation, the anchor 26 may comprise an internally-threaded compression nut. In one embodiment, the anchor 26 may be thirteen (13) millimeters in length, as measured from the first end to the second end of the anchor 26, and may be 6.5 millimeters in diameter, as measured at the meeting of the enlarged shoulder 30 with that portion of the anchor configured to fit into a bored bone (as described in detail below).

Figure 1C:
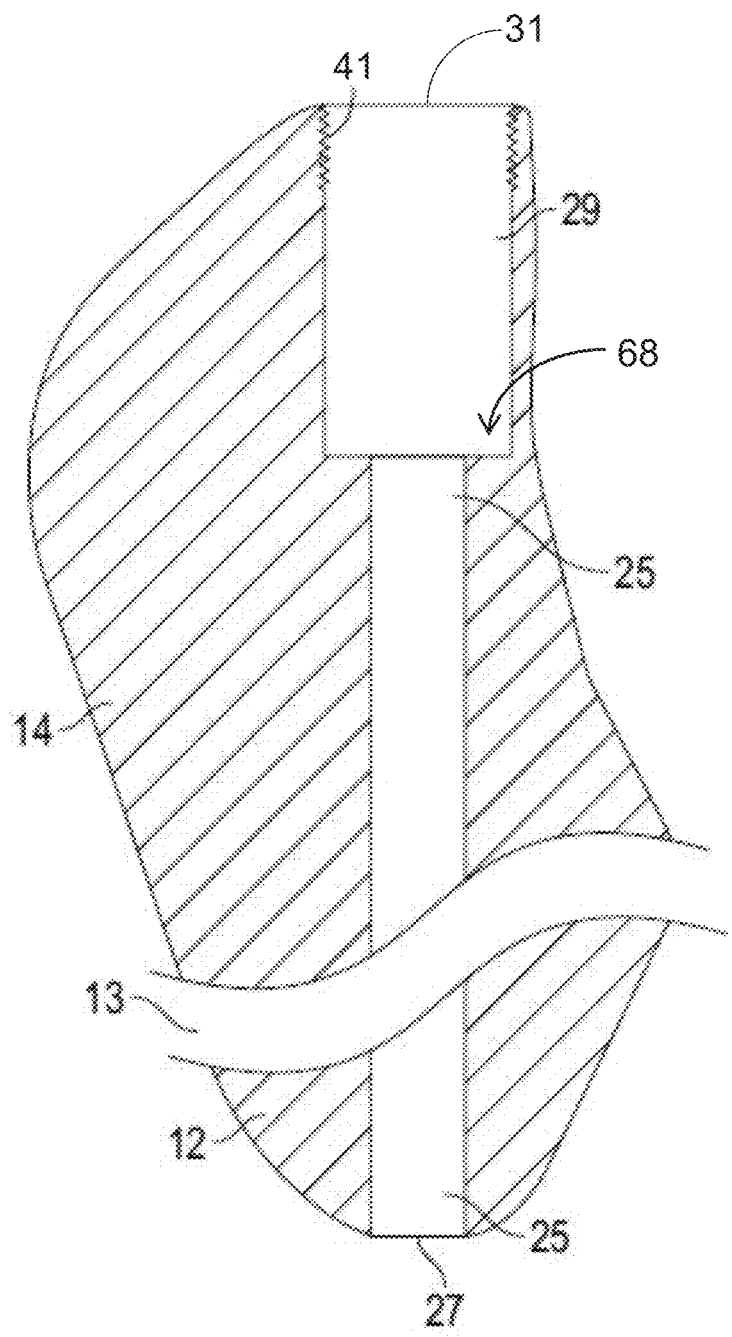
FIG. 1C is a cross-section view of the two bone fragments of FIG. 1A along the section 2-2 without the bone compression device of FIG. 1A.

Referring additionally to FIGS. 1B and 1C, the fastener 16 may be insertable into the first 12 and second 14 bone fragments, and the anchor 26 may be insertable into the second bone fragment 14. When assembled and tightened together, the head portion 20 of the fastener 16 and the shoulder 30 of the anchor 26 may operate to compress the bone fragments 12, 14 together to close and compress the fracture 13. For example, and without limitation, with more particular reference to FIG. 1C, the fastener 16 may be configured to insert through a first bore 25 formed in both the first 12 and second 14 bone fragments. The shank portion 18 may extend through the first bone fragment 12 and into the second bone fragment 14. Upon insertion, the head portion 20 of the fastener may engage a rim 27 of the first bore 25 to prevent the fastener 16 from further entering the bone fragments 12, 14. The anchor 26 may be configured to insert into a second bore 29 having a larger diameter than that of the first bore 25, and that may be formed in the second bone fragment 14. The anchor shoulder 30 may engage a rim 31 of the second bore 29 so that, as the fastener 16 and anchor 26 are tightened together, the anchor shoulder 30 and the fastener head portion 20 may transmit compressive force to the bone fragments 12, 14 about the respective bore rims 27, 31 to compress the first 12 and second 14 bone fragments together. Also for example, and without limitation, the length of the threaded shank portion 22 may be short enough to be substantially received within the anchor 26 so as to largely avoid the threaded area 22 presenting stress concentrations with bone of the first bone fragment 12.

According to some embodiments, the second bore 29 may be coaxial with the first bore 25, and may have a substantially greater diameter than the first bore 25. In addition, the first 25 and second 29 bores may be formed with respective diameters that are the same or very slightly larger than the fastener shank 18, 22 and the outside diameter of the anchor 26, respectively. Accordingly, the outside diameter of the anchor 26 may be substantially greater than the outside diameter of the shank portion 18 of the fastener 16 according to some embodiments. For example, and without limitation, a snug press fit both of the fastener shank 18 in the first bore 25 and of the anchor 26 in the second bore 29 may be provided to advantageously facilitate the assembled compression device 10 being held tightly and motionless within the compressed bone fragments 12, 14. One skilled in the art will appreciate that various changes, adaptations, and modifications may be made without departing from the spirit of the invention and the scope of the appended claims. For example, and without limitation, a smaller compression system may comprise a fastener shank 18 having a diameter of 3 millimeters and a receiving anchor 26 having a diameter of 4.5 millimeters. Also for example, and without limitation, a larger compression system may comprise a fastener shank 18 having a diameter of 6 millimeters and a receiving anchor 26 having a diameter of 8.5 millimeters.

In certain embodiments of the invention, the bone compression device 10 may serve not only to advantageously compress bone fragments together (e.g., reduce a fracture and hold fractured surfaces together for healing), but also, due to the rigid nature of the device, to advantageously support the reduced fracture against bending stresses encountered by the first 12 and second 14 bone fragments. For example, and without limitation, when placed within a patella, the device 10 may support the patella fragments 12, 14 against forces by the quadriceps and patella tendons that otherwise may cause the fracture 13 to open anteriorly. In such an embodiment, the bending moment particularly could be in the vicinity of the fracture line 13, and thus the bone compression device 10 may be configured to be quite strong and resistant to bending moments at this location (e.g., wishboning). In addition, most transverse fractures occur in the lower (distal) one-third of the patella. In such an embodiment, the fastener 16 may be passed through the smaller bone fragment 12 into the larger bone fragment 14 for the advantage of added strength.

Referring again to FIGS. 1C, 2A-2C, and 3, the anchor 26 may comprise an externally-threaded portion 23 configured to engage bone, for example, and without limitation, at an inner surface portion 41 of the second bore 29 so as to advantageously gain better purchase of the anchor 26 to the bone fragment 14. The inner surface portion 41 may be threaded complementarily to the threaded portion 23 of the anchor 26. For example, and without limitation, the threading 41 of the inner surface of second bore 29 may be accomplished using one or more thread-cutting tools, such as serial taps and/or nut taps. Also for example, and without limitation, the threaded portion 23 of the anchor 26 may be configured for self-tapping (e.g., characterized by a flute and cutting edge similar to those on a tap). In one embodiment, the threaded portion 23 of the anchor 26 may begin approximately adjacent to the shoulder 30 and may extend up to one half the length of the anchor 26.

In some embodiments, the bone compression device 10 may include one or more washers. Referring to FIGS. 2A-2C and 3, for example, and without limitation, a first washer 36 may be provided that may be configured to be positioned fittedly about a perimeter of the anchor 26, such that the washer 36 may simultaneously engage the rim 31 of the second bore 29 and the shoulder 30 of the anchor 26 to advantageously transmit and spread the compressive force from the anchor shoulder 30 about the rim 31 of the second bore 29. Also for example, and without limitation, a second washer 38 may be configured to be positioned fittedly about a perimeter of the shank 18 of the fastener 16 to simultaneously engage the head portion 20 of the fastener 16 and the rim 27 of the first bore 25 to advantageously transmit and spread the compressive force from the head portion 20 about the rim 27. In some embodiments, the first and second washers 36, 38 may be integrally formed as part of the anchor shoulder 30 and the fastener head portion 20, respectively.

Figure 7A:
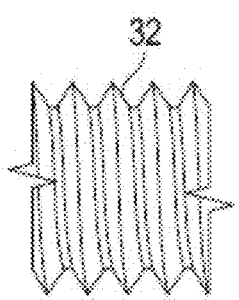
FIG. 7A is a side view of a locking screw according to an embodiment of the present invention.
Figure 7B:
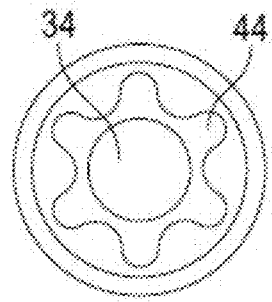
FIG. 7B is an end view of the locking screw of FIG. 7A.

Referring to FIG. 2C and FIG. 3 and also FIGS. 7A and 7B, according to one embodiment, the bone compression device 10 may include a lock that may be positioned within the anchor bore 28 and may be adapted to lock the fastener 16 and anchor 26 against relative rotation. For example, and without limitation, the lock may include at least one of a locking screw and a lock nut. In one embodiment, the lock may be in the form of an externally-threaded lock nut having an internally-threaded bore. The lock nut may be threadedly received within the anchor bore 28. For example, and without limitation, the end of the threaded fastener portion 22 may be slightly smaller in diameter than the anchor bore 28 so as to be received within the bore of the lock nut. The lock nut may then be tightened against the end of fastener 16 to lock the position of the fastener 16 within the anchor 26.

In one embodiment, the lock may be in the form of an externally-threaded locking screw 32 having an internal bore 34. For example, and without limitation, the locking screw 32 may comprise a cannulated, externally-threaded bolt section. The locking screw 32 may be receivable within the internally-threaded bore 28 of the anchor 26 and may be configured to be advanced coaxially against the confronting end of the threaded shank portion 22 to lock the position of the shank portion 22 within the anchor 26. Thus, when the bone compression device 10 is deployed within host bone fragments, the locking screw 32 may advantageously prevent the anchor 26 and the fastener 16 from inadvertently disengaging (for example, under stress or movement). For ease of understanding, the following description refers to the lock as the locking screw 32.

The bone compression device 10 may comprise a biocompatible material according to some embodiments. For example, and without limitation, the fastener 16, the anchor 26, and the locking screw 32 may comprise titanium and/or other biologically acceptable metal. In some embodiments, the threaded shank 22 of the fastener 16, the thread of the locking screw 32, and/or the internal thread in the anchor bore 28 of the anchor 26 each may comprise a material that may deform slightly under exerted pressure. For example, and without limitation, as the fastener 16 and locking screw 32 are tightened against each other, one of the pieces may deform slightly so as to lock the fastener shank 22 within the anchor's threaded bore 28. In some embodiments, the bone compression device 10 may include a deformable insert (not depicted) placed within the anchor bore 28 between the end of the threaded fastener shank 22 and the locking screw 32. As the pieces are tightened together, the insert may deform, thus locking the position of the shank 22 and the anchor 26. In some embodiments, the deformable insert may comprise a biocompatible polymer.

Referring now to FIGS. 4-8, detailed views of the individual components of the bone compression device 10 are illustrated according to some embodiments. For example, and without limitation, one or more of the fastener head portion 20, the anchor second end near the shoulder 30, and the locking screw 32 may include a drive portion that may accept a twisting tool, such as a screwdriver, to threadedly advance and/or withdraw the component. For example, and without limitation, the fastener head portion 20 may include a recessed drive portion 40, the anchor 26 may include a recessed drive portion 42, and the locking screw 32 may include a recessed drive portion 44. In the embodiments shown, the drive portions may be configured as hexalobular recesses with a bore through the center of the drive portions. Other drive configurations may also be used, as the invention is not restricted to hexalobular drives. In particular, raised or recessed drive surfaces, such as would fit a (e.g., hexagonal) wrench may also be used.

In some embodiments, three different sizes of recessed drive portions (e.g., hexagonal depressions) may be used. The screwdriver that fits the head portion 20 of the fastener 16 may have a ratcheting mechanism such that when the fastener 16 is tightened within the anchor 26, the anchor 26 may be held from turning by one screwdriver, and the other screwdriver, with a ratcheting mechanism, may be used to turn the fastener 16 into the threaded bore of the anchor 28. In some cases, a screwdriver with a hollow bore and a large hex head on its end may be used. A smaller screwdriver, having a smaller hex head, may then fit through the larger screwdriver and may fit the locking screw 32.

Figure 6A:
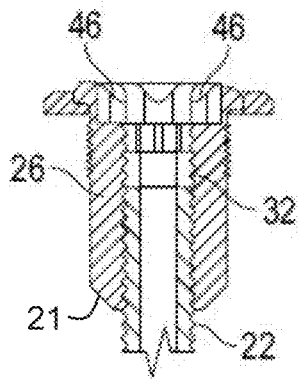
FIG. 6A is a partial cross-section view of an assembled anchor, fastener and locking screw according to an embodiment of the present invention.
Figure 6B:
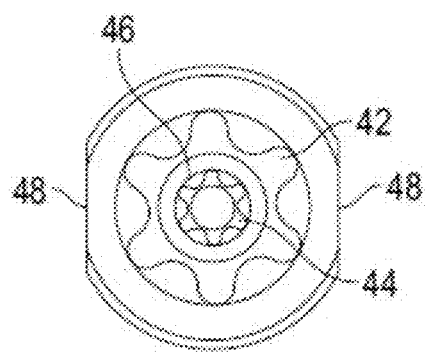
FIG. 6B is a top view of the assembly of FIG. 6A.

Referring additionally to FIG. 6B, in one embodiment, the anchor drive portion 42 may extend about the circumference of the anchor's 26 second end while providing access to the locking screw drive portion 44 through the anchor bore 28. As illustrated in FIGS. 6A and 6B, for example, and without limitation, the anchor 26 may include a small, inwardly-protruding internal lip 46 at the end of the anchor bore 28 at the second end of the anchor 26. For example, and without limitation, the lip 46 may be formed integrally with the anchor 26, and may advantageously prevent the locking screw 32 from being turned out of the anchor 26 through the second end. Thus, in the event that the locking screw 32 becomes loose after the bone compression device 10 is installed, the lip 46 may prevent the locking screw 32 from breaking loose into the surrounding body. In some embodiments, the lip 46 may be rounded and may extend around the entire inner circumference of the anchor bore 28. In certain embodiments, however, the lip 46 may be discontinuous, and/or squared, as desired for a particular implementation. The lip 46 may extend inwardly enough to contact the locking screw 32, but not enough to interfere with the drive portion 44 of the locking screw 32.

Figure 8A:
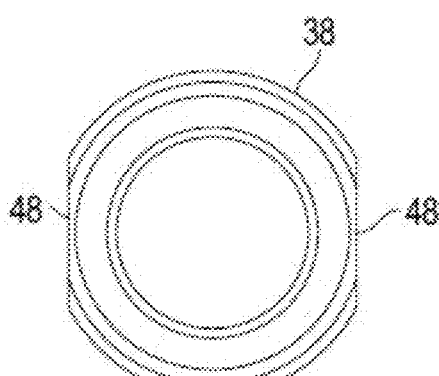
FIG. 8A is a front view of a washer according to an embodiment of the present invention.
Figure 8B:
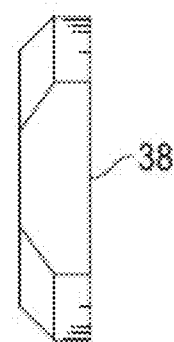
FIG. 8B is a side view of the washer of FIG. 8A.
Figure 8C:
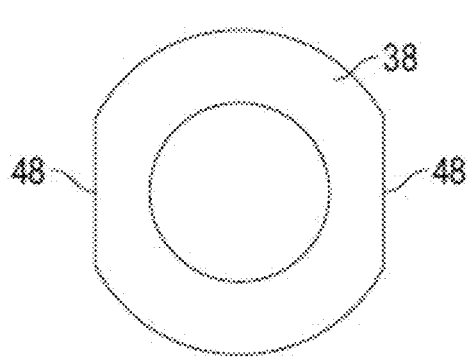
FIG. 8C is a back view of the washer of FIG. 8A.
Figure 9A:
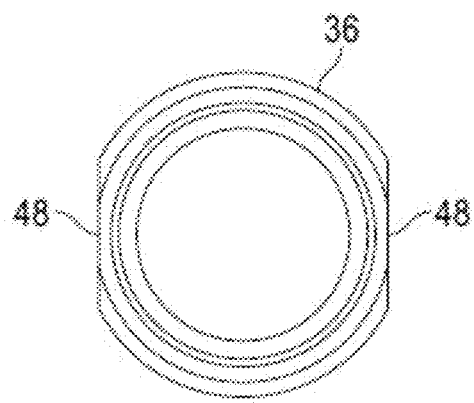
FIG. 9A is a front view of a washer according to an embodiment of the present invention.
Figure 9B:
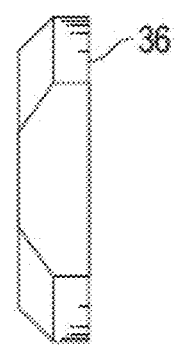
FIG. 9B is a side view of the washer of FIG. 9A.

FIGS. 8A-8C illustrate various views of an exemplary embodiment of the washer 38 that may be configured for positioning about the fastener head portion 20. FIGS. 9A and 9B illustrate a top and side view of the washer 36 that may be configured for positioning about the anchor 26. As illustrated in the referenced figures, the washers 36, 38, and, for that matter, the fastener head portion 20 and the shoulder 30 of the anchor 26 (FIG. 5B), may be characterized by diametrically opposed flat surfaces 48 that may be rotationally positioned so as to reduce the extent to which ends of the device 10 may protrude from the bore holes 25, 29.

Referring additionally to FIGS. 18A, 18B, 19A, 19B, 20A, 20B, 21A, and 21B, the surfaces of the washers 36, 38, and the fastener head portion 20 and the anchor shoulder 30 that these washers 36, 38 meet, may be advantageously shaped for application-specific purposes. For example, and without limitation, a washer 36, 38 may be chamfer-shaped to reduce stress concentrations (FIGS. 19A, 19B). Also for example, and without limitation, top surfaces of the washers 36, 38 may present a substantially flat section 33, 35 against which a substantially flat compression surface of the fastener head portion 20 and/or the anchor shoulder 30 may apply compressive force for transition, by the washer 36, 38, to a non-planar bone surface (FIGS. 18A, 18B, 19A, 19B, 20A, 20B). Also for example, and without limitation, washers 36, 38 may be curve-shaped (FIGS. 18A, 18B), wedge-shaped (FIGS. 20A, 20B), and/or otherwise customized in shape and/or size to the available bone surface to which compression force is to be advantageously distributed. More specifically, for large-bone procedures, such as immobilization of femur fracture and fusion of the Sacroiliac joint, shape customization and upsizing may cause a washer 36, 38 to operate as a plate, thereby advantageously delivering compression across larger areas of bone. Also for example, and without limitation, washers 36, 38 may be characterized by a countersink 39 configured to receive the fastener head portion 20 and/or the anchor shoulder 30 so as to advantageously minimize soft tissue irritation by the deployed device 10 (e.g., fastener head portion 20 and/or anchor shoulder 30 not left proud), and thereby to generate less need to remove the device 10 once deployed.

Embodiments of the bone compression device 10 may be used to fix a wide variety of bone fractures, including fractures of the patella. For example, and without limitation, the device 10 may be used to secure the calcaneus, the distal femur, the tibia plateau (e.g., using metal plates), the ankle syndesmosis, and the distal humerus, as well as periprosthetic fractures around total knee arthroplasties and tibiofibular bone bridging (Ertl) during a below-knee amputation (BKA). For ease of understanding of the following description, the device 10 is described herein as being deployed within the patella with the anchor 26 positioned at the proximal (upper) end of the patella.

Figure 10:
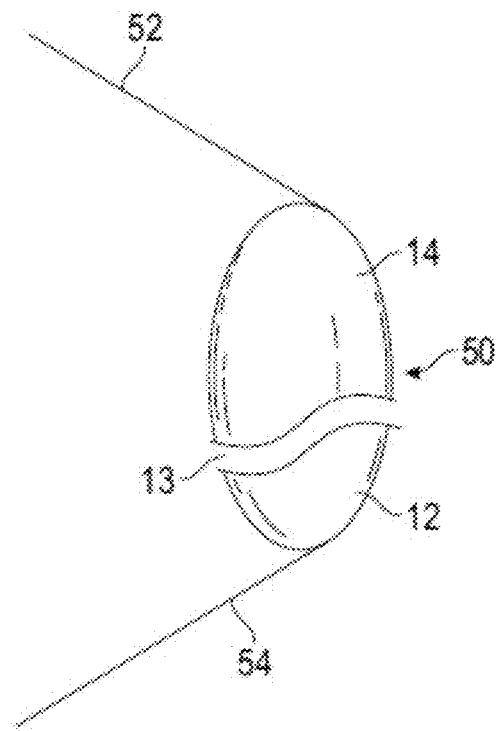
FIG. 10 is a schematic illustration of a fractured patella.

Referring now to FIG. 10, a schematic illustration of a fractured patella 50 is shown. The patella 50 is normally supported at the knee by a quadriceps tendon 52 from above and a patellar tendon 54 from below, the latter being inserted in the tibia. The patella 50 is supported near its middle by contact with an intercondylar groove of the femur. In use, the patella 50 may be subjected to substantial bending moments as the knee is bent and weight is placed on the leg. Breakage of the patella under these conditions generally is transverse (that is, side-to-side) with the patella itself tending to open up anteriorly. When deployed to repair the patella 50, two spaced bone compression devices 10 may be used for rather common transverse fractures (as illustrated in FIG. 10 from the side). In the case of fixing a longitudinal fracture, in some embodiments only one bone compression device 10 may be needed.

According to some embodiments, the bone compression device 10 may be used in one or more methods of fixing two or more bone fragments. For example, and without limitation, a device 10 may be installed through a general knee surgery, in which the patella is laid open through a generally mid-line, longitudinal incision. In a less invasive method, the proximal and distal ends of the patella can be accessed through small incisions. Similar open and subcutaneous procedures may be performed to address fractures of bones other than the patella.

Figure 11:
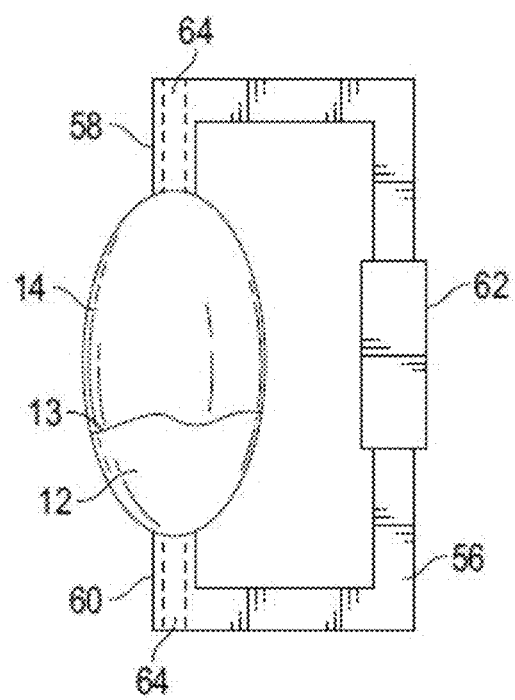
FIG. 11 is a schematic illustration of the fractured patella of FIG. 10 showing use of a clamp to reduce the fracture according to an embodiment of the present invention.

Referring now to FIG. 11, in certain embodiments the surgical procedure may begin by temporarily fixing the first and second bone fragments 12, 14 with a clamp 56, such as a C-clamp having cannulated jaws. The clamp 56 generally may include first and second jaws 58, 60 configured for contacting the fractured pieces of bone, an adjustment mechanism 62 for opening and closing the jaws, and a small cannula 64 extending through the jaws. Although perhaps only two bone fragments may result from a simple fracture, if the patella has been injured by a crushing load, sometimes more fragments may be formed and must be fit and held together. For this purpose, a C-clamp 56 may be employed to fix the pieces in their correct position while the bores are being formed through the patella.

Figure 12:
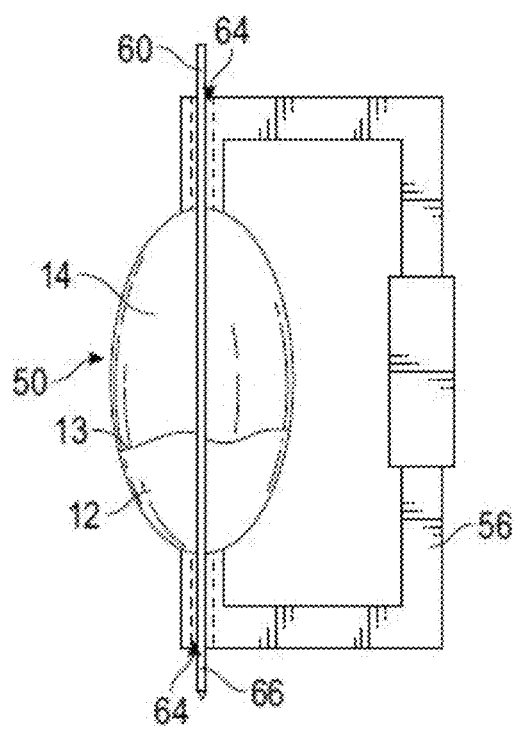
FIG. 12 is a schematic illustration of a Kirschner wire within the fractured patella shown in FIG. 11 according to an embodiment of the present invention.

FIG. 12 illustrates the use of a Kirschner or "K" wire 66 to start a bore hole through the first and second bone fragments 12, 14. For example, and without limitation, the K wire 66 may be characterized by a diameter of 2.0 millimeters. According to this embodiment, the patella 50 may be prepared by passing the stiff straight wire 66 through the first bone fragment 12, across the fracture line, and through the second bone fragment 14, such that the wire 66 is placed where the bone compression device 10 is subsequently to be placed. In some embodiments, insertion of the K wire 66 may be guided by the cannulated C-clamp 56, as shown in FIG. 12. For example, and without limitation, in some embodiments the jaws 58,60 of the clamp 56 may include one or more removable inserts with varying sized bores. The inserts with the smallest bore may guide the K wire 66, the next largest inserts may guide a drill, and larger inserts may guide insertion of the anchor 26 and/or fastener 16 into the bone fragments 12, 14. The bored inserts may be nested within the jaws in some cases.

Referring now to FIG. 13, guided by the wire 66, a cannulated bone drill may be used to drill the first bore 25 (see FIG. 1C) through the first bone fragment 12 and into the second bone fragment 14 in the proximal direction (that is, upwardly as shown in FIG. 13). The diameter of the first bore 25 may be very slightly larger than the diameter of the threaded fastener shank portion 22, thereby advantageously providing for a snug press fit of the fastener 16 in the first bore 25. From the proximal end of the second bone fragment 14, and again guided by the K wire 66, another, substantially larger second bore 29 may be drilled downwardly into the second bone fragment 14 for a predetermined distance, and coaxial with the first bore 25.

In some embodiments, the larger drill for this second bore 29 may be characterized by an end portion terminating in a squared-off end that may create the second bore 29 as a counterbore characterized by a cylindrical cavity having a squared-off floor 68. One of ordinary skill in the art will appreciate that the present invention may be similarly carried out by employing drill end portions of varying shapes to provide a counterbore floor 68 characterized as rounded, chamfered, tapered, stepped, or other mill types known in the art. In some embodiments, the larger drill may be characterized by an enlarged, annular shoulder spaced from its tip to limit the distance to which the drill may penetrate into the second bone fragment 14. If desired, the annular shoulder may define a drilling surface configured to produce a short countersunk (or counterbored) depression 70 at the rim of the second bore 29 to receive the enlarged shoulder 30 of the anchor 26, or the washer 36 if a washer is used. Similarly, in some embodiments, the drill for the first bore 25 may produce a short countersunk (or counterbored) depression 72 at the rim 27 of the first bore 25 to receive the fastener head portion 20 or the washer 38 if one is used. In some embodiments, the washers 36, 38 may be eliminated, particularly when small patients are being treated. If only one washer is to be used, that washer 38 may be placed on the fastener 20 side. In some cases, as described above, the washers 36, 38 may include flat opposing edges that may be rotated to limit protrusion of the fastener 16 from the first bore 25 and/or the anchor 26 from the second bore 29.

Figures 15, 16:
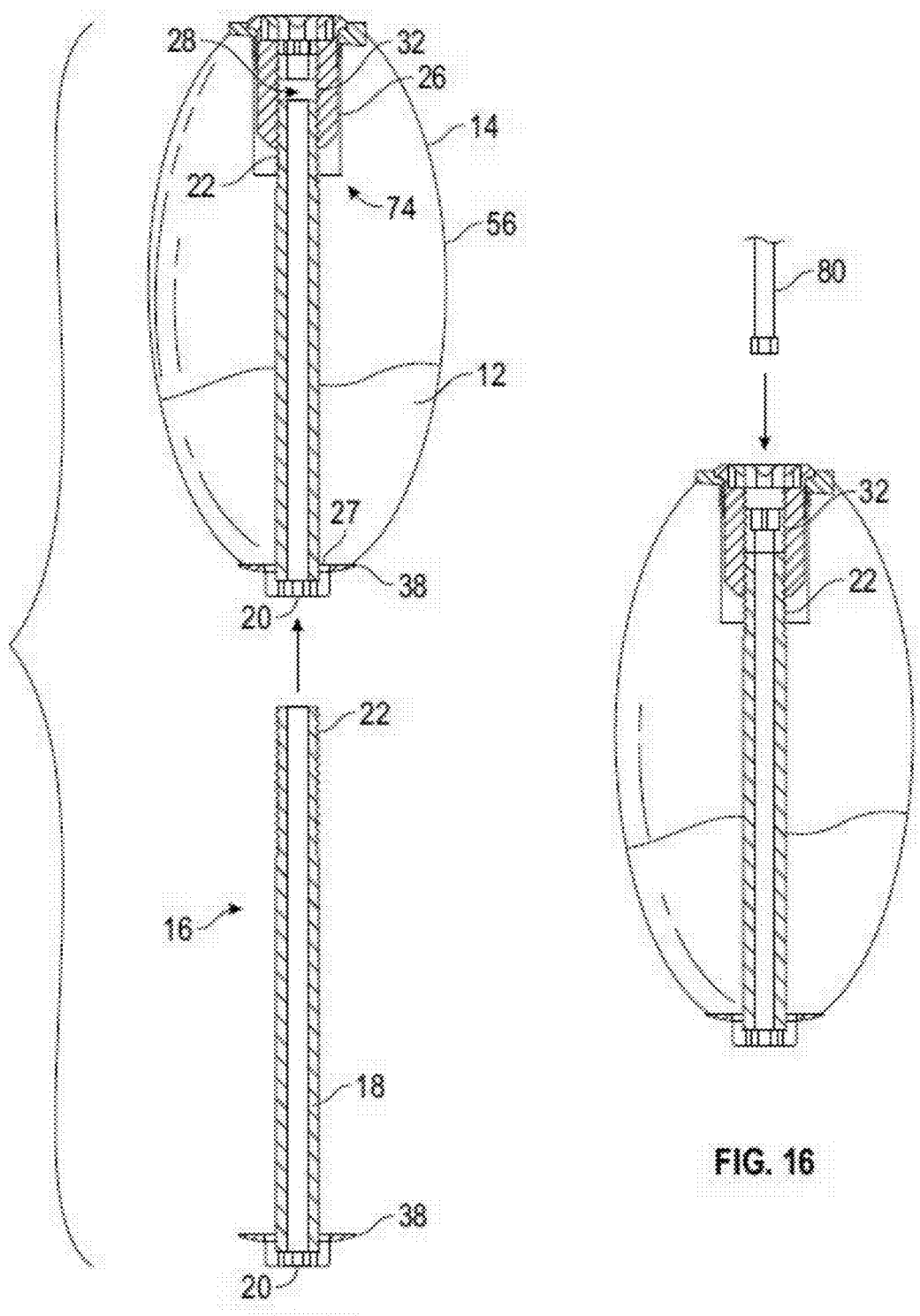
FIG. 15 illustrates the insertion of an elongated fastener into a bore formed in the patella of FIG. 13 according to an embodiment of the present invention.
FIG. 16 illustrates the tightening of a locking screw using a twisting tool according to an embodiment of the present invention.
Figure 16A:
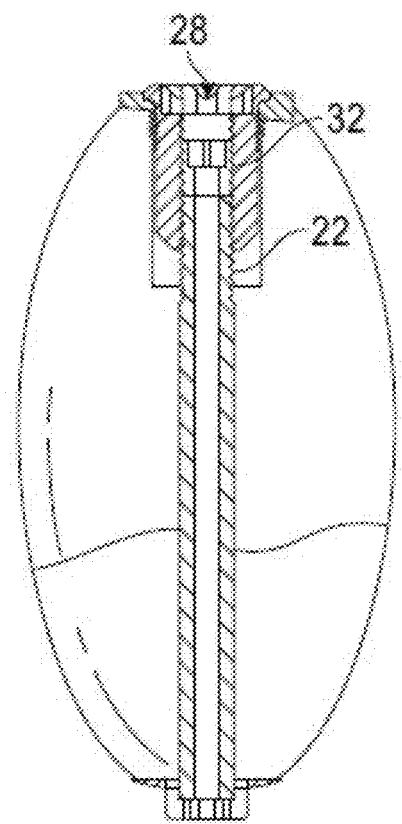
FIG. 16A illustrates seating of the locking screw of FIG. 16 according to an embodiment of the present invention.

Referring to FIG. 14, the first end of the anchor 26 may be inserted into the second bore 29 such that the anchor shoulder 30 may engage the rim 31 of the second bore 29. For example, and without limitation, the first end of the anchor 26 may be chamfered 21 or rounded (not shown) to advantageously facilitate gentle insertion of the anchor 26 into the second bore 29. The anchor 26 may contain within it the locking screw 32. As illustrated in FIG. 14, the washer 36 may provide an intermediate surface through which the shoulder 30 may engage the rim 31. Referring additionally to FIG. 15, the fastener 16 may be inserted through the first bore 25 and into the second bore 29. The fastener 16 may be advanced so that the externally-threaded portion 22 of the fastener shank portion 18 may thread into the anchor bore 28. The fastener head portion 20 may engage the rim 27 of the first bore 25, in this case, through the washer 38. As the fastener 16 and the anchor 26 are turned in opposite directions relative to each other in a tightening manner, the fastener 16 and anchor 26 may compress the first 12 and second 24 bone fragments together to secure the fracture 13. In some embodiments, a surgeon may estimate the amount of needed pressure/compression simply by tightening the fastener 16 and anchor 26 by hand. In other embodiments, a torque-measuring or torque-limiting device may be used, although these devices are not necessarily required to practice the invention disclosed herein.

Referring now to FIGS. 14, 15, 16, and 16A, it should be understood here that the anchor 26, when positioned in the second bore 29, may exert compressive force against the second bone fragment 14 through contact of the annular shoulder 30 (or the washer 36, if used) with the rim 31 of the second bore 29, and not through contact of the confronting surface (counterbore floor) 68 of the large bore 29 and the first end of the anchor 26. These surfaces desirably may be separated by a small space 74, so as to so as to advantageously avoid the anchor 26 presenting stress concentrations with bone of the milled floor 68 of the large bore 29. For example, and without limitation, the small space 74 may measure up to three (3) millimeters in width in some embodiments. Also for example, and without limitation, the small space 74 may be any non-flush distance, defined as a minimum gap required to prevent contact of the anchor 26 with the counterbore floor 68 based on a bending moment of the bone surrounding the large bore 29.

Referring to FIG. 16, the fastener 16 and the anchor 26 may be threaded together to provide the desired compression. The locking screw 32 may be advanced coaxially through the anchor bore 28 towards the threaded end 22 of the fastener 16. A twisting or driving tool 80, such as a screwdriver, may be used to advance the locking screw 32. The locking screw 32 may be turned tightly into the end of the fastener 16 to lock the position of the fastener 16 relative to the anchor bore 28. In some embodiments, turning the locking screw 32 into the fastener end may deform the locking screw and/or the fastener end or the threads of either or both in order to more securely lock the fastener 16 in place to prevent it from backing out of the first bore 25.

As stated herein, in some embodiments, the anchor 26 may include an internal lip 46 configured to prevent the locking screw 32 from backing out of the second bore 29. In such an embodiment, the locking screw 32 may be inserted into the first end of the anchor 26 prior to inserting the anchor 26 into the second bore 29. In other embodiments, the locking screw 32 may simply be inserted turnedly into the anchor bore 28 through the second (exterior) end of the anchor 26 when no lip is included.

In some embodiments, the surgical procedure of deploying the device 10 may include a step of selecting a fastener 16 of appropriate length from a plurality of fasteners of different lengths, the plurality of fasteners being included in a kit (as described in more detail below). For example, and without limitation, the anchor 26 may be inserted into the larger second bore 29, with its shoulder 30 or washer 38 in contact with the rim 31 of the bore 29 and with the locking screw 32 threadedly received by and approximately flush with the exterior end of the anchor bore 28. A surgeon may then use a measuring rod to determine the distance between the rim 27 of the smaller bore 25 and the confronting end of the locking screw 32. An appropriate fastener 16 may be chosen from the kit having a length such that the end of the threaded shank portion 22 may be spaced slightly from the confronting end of the locking screw 32 when the fastener 16 may be threaded into the anchor 26 and the desired compression of the fracture edges of the bone may be achieved. The locking screw 32 may then be threaded further into the anchor bore 28 into locking engagement with the end of the fastener 16, so as to advantageously prevent the fastener 16 from backing out of the bore 25.

Most fractures of the patella are transverse to the long direction of the leg, due at least in part to the forces on the patella exerted by the quadriceps and patellar tendons and the geometry of the patella/femoral condyles. In some embodiments of the present invention, a surgical procedure for deploying the device 10 may include providing a second (or even a third) bone compression device which may then be inserted into the first and second bone fragments 12, 14 across the fracture 13 and spaced a distance away from the first bone compression device 10.

Figure 17:
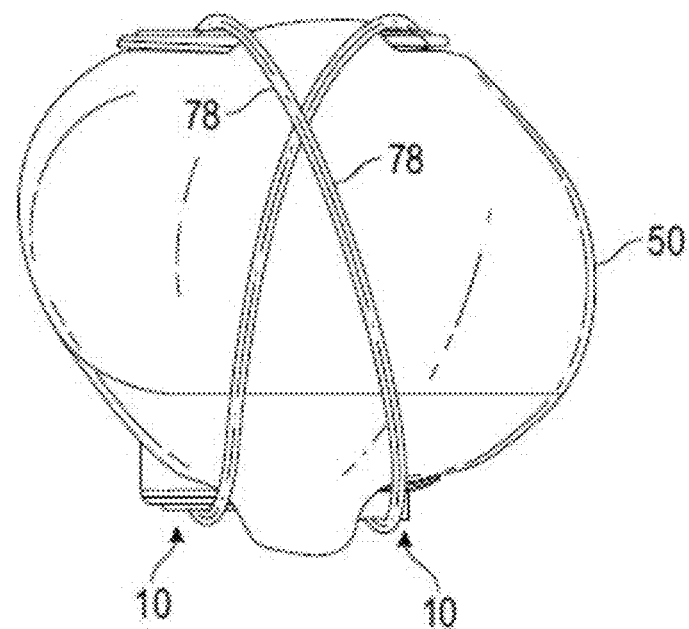
FIG. 17 is a schematic illustration of a fractured patella stabilized by tension bands and two bone compression devices according to an embodiment of the present invention.
Figure 22:
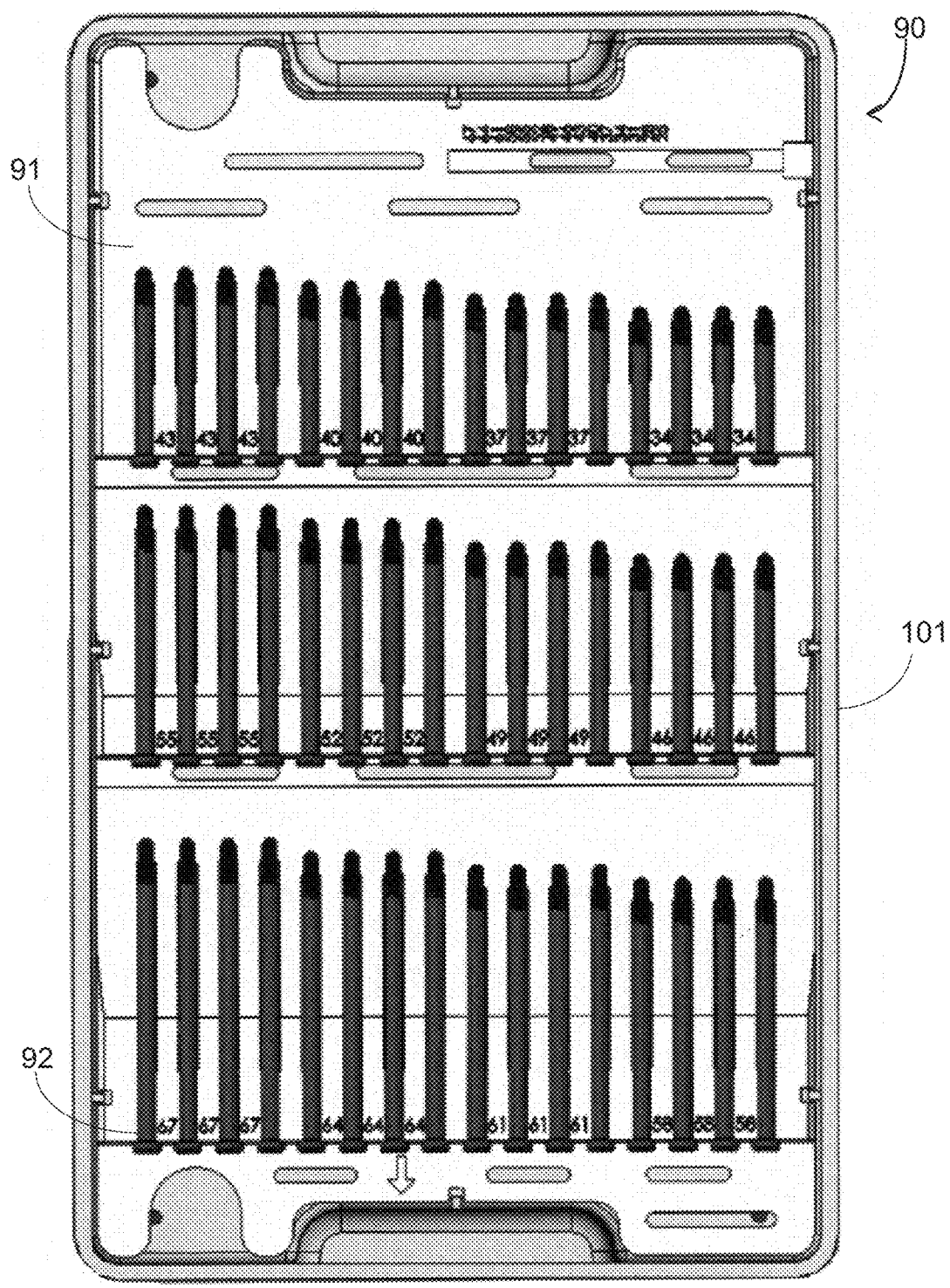
FIG. 22 is a front view of according to an embodiment of the present invention.
Figure 23:
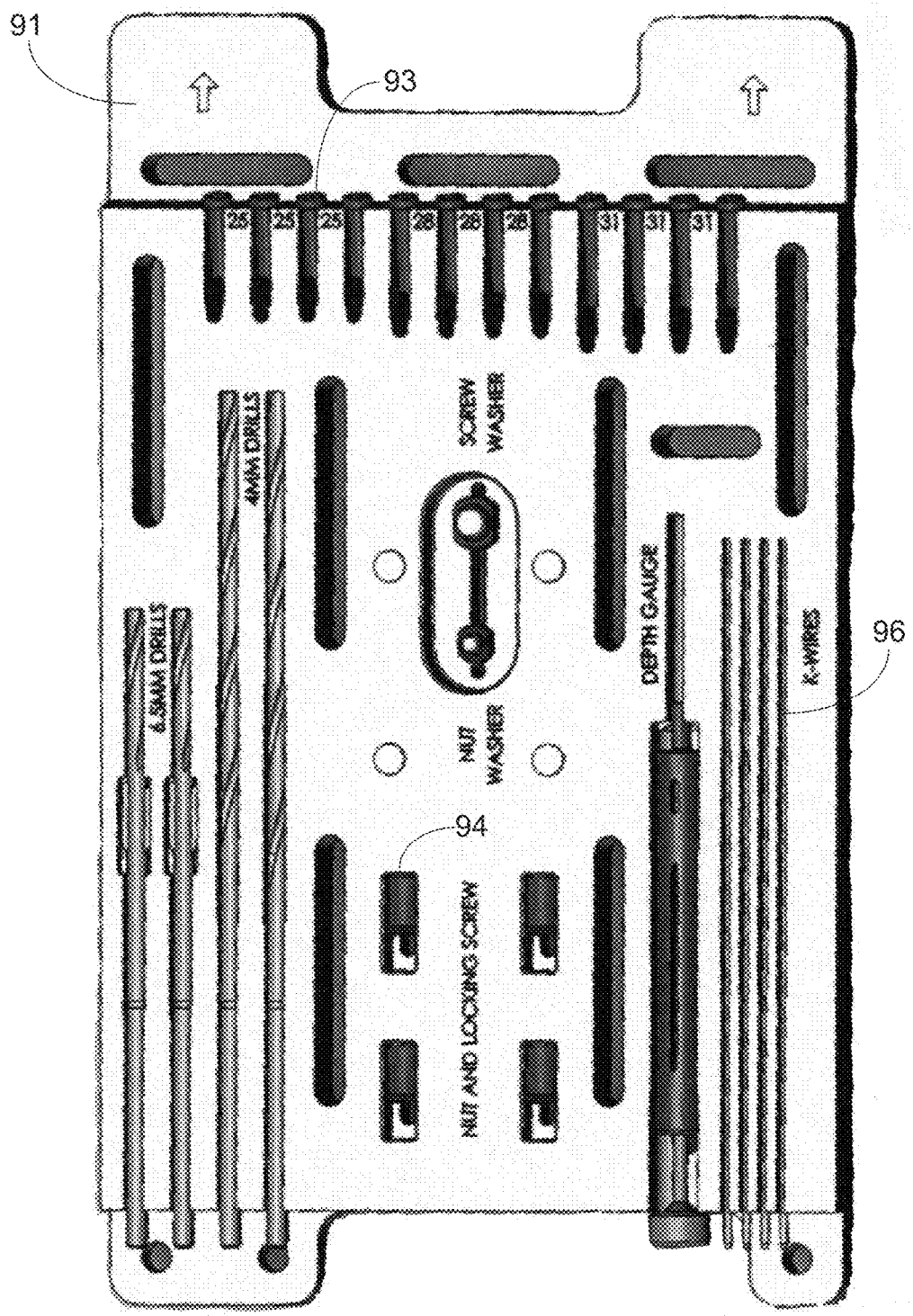
FIG. 23 is a front view of according to an embodiment of the present invention.
Figure 24:
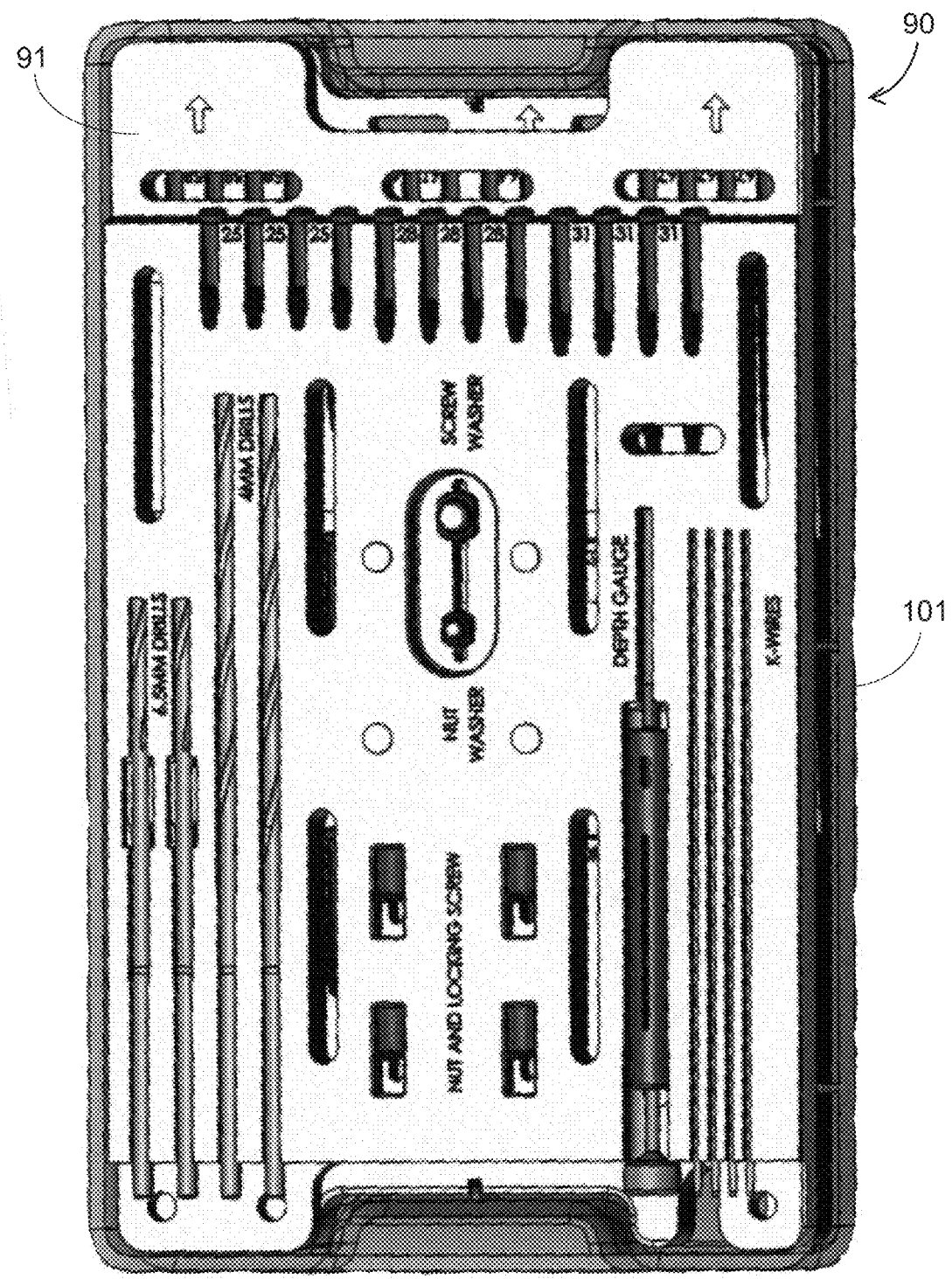
FIG. 24 is a front view of according to an embodiment of the present invention.
Figure 25:
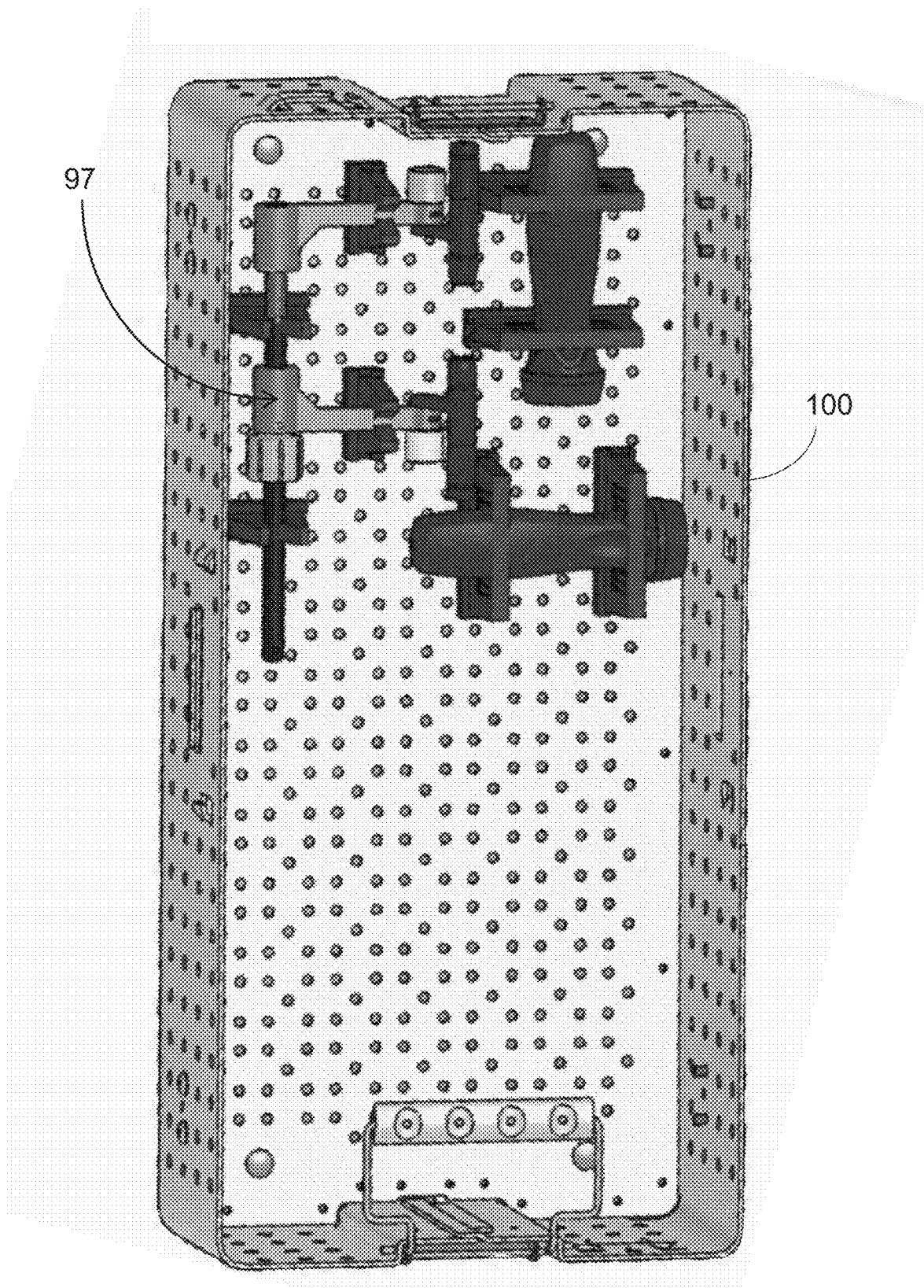
FIG. 25 is a perspective view of according to an embodiment of the present invention.
Figure 26:
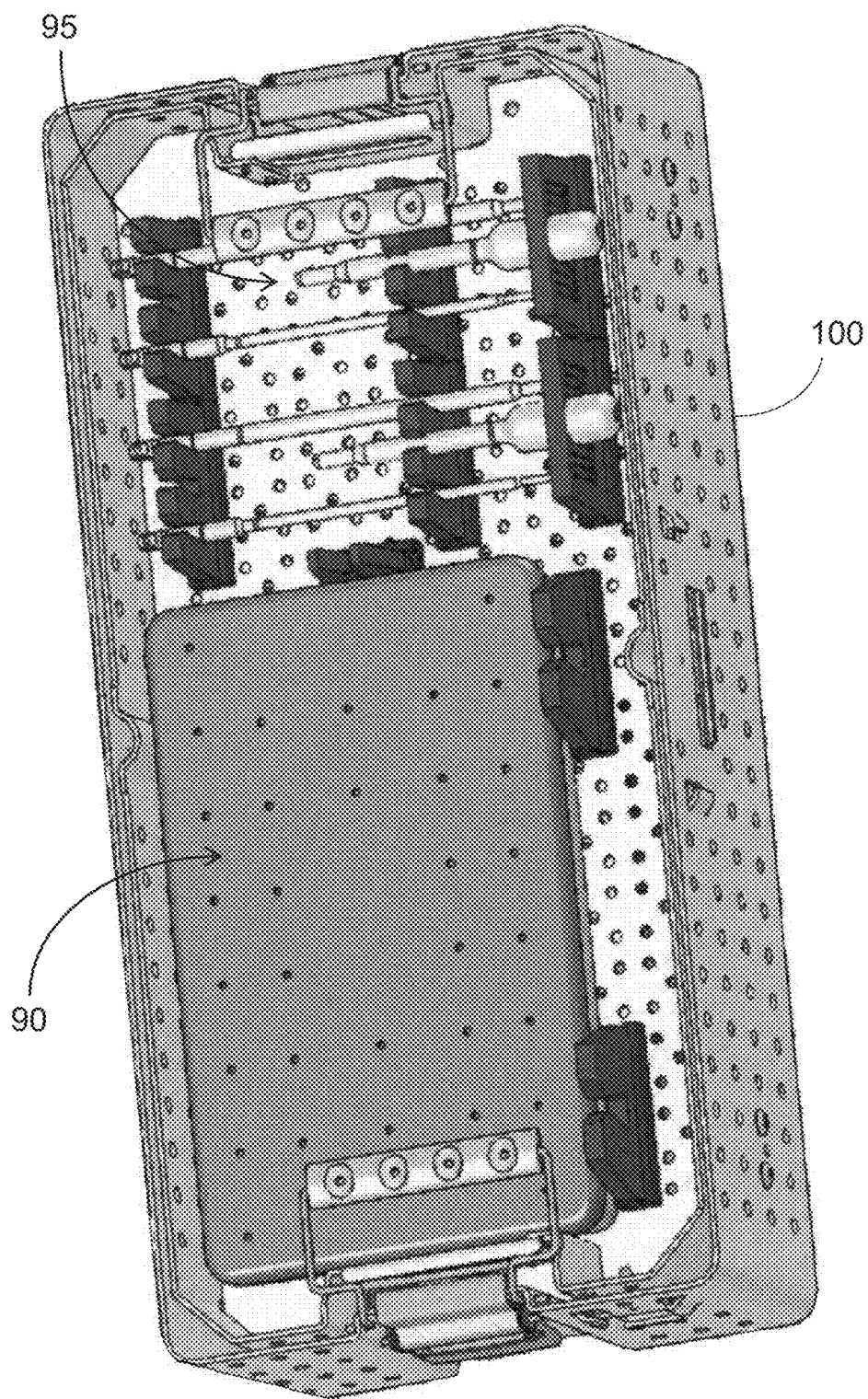
FIG. 26 is a perspective view of according to an embodiment of the present invention.

After placing and tightening one or more bone compression devices, the bone fragments 12, 14 may not yet be completely stabilized. For example, and without limitation, movement between some of the patella fragments may yet occur. Referring now to FIG. 17, to advantageously reduce the tendency for movement, various surgical wires 78 may be passed through the open interiors of the bone compression devices, and may be appropriately strung together, as in a figure eight configuration, to further immobilize the patella. Such a method may include using cerclage wires to further stabilize the fracture. In some embodiments, the wires may be fed into place using tools, so that the whole operation may be performed through small incisions.

In addition to a bone compression device 10 and method of installing and using bone compression devices, in some embodiments the invention provides one or more kits for compressing together first and second bone fragments. Referring now to FIGS. 22-26, for example, and without limitation, a kit may comprise a caddy 90 that may include some number of trays 91 configured to carry and organize a plurality of fasteners 16, such as those previously described, having different lengths (e.g., ranging as illustrated 92, 93 from 25 millimeters to 67 millimeters in 3 mm increments), along with Kirschner wires 96, tension bands, and/or at least one anchor 26 with a lock 32 (e.g., externally-threaded locking screw) as illustrated at 94. In other embodiments, a caddy 90 may further include a deformable insert, receivable within the anchor bore between the second end of the fastener shank and the locking screw, to deform and lock the position of the fastener shank when the fastener shank and the locking screw are tightened against each other. In some embodiments, a kit may further comprise an instrument case 101 configured to carry and organize the caddy 90 as well as multiple driving tools 95 and/or a cannulated clamp 97.

Thus, embodiments of the present invention are disclosed herein. Although the present invention has been described in considerable detail with reference to certain disclosed embodiments, the disclosed embodiments are presented for purposes of illustration and not limitation and other embodiments of the invention are possible. One skilled in the art will appreciate that various changes, adaptations, and modifications may be made without departing from the spirit of the invention and the scope of the appended claims. For example, and without limitation, the plurality of fasteners 16, such as those previously described, may have shorter lengths ranging from 14 millimeters to 24 millimeters in 2 mm increments, and/or may have longer lengths ranging from 70 millimeters to 120 millimeters in 5 mm increments.

Some of the illustrative aspects of the present invention may be advantageous in solving the problems herein described and other problems not discussed which are discoverable by a skilled artisan. While the above description contains much specificity, these should not be construed as limitations on the scope of any embodiment, but as exemplifications of the presented embodiments thereof. Many other ramifications and variations are possible within the teachings of the various embodiments. While the invention has been described with reference to exemplary embodiments, it will be understood by those skilled in the art that various changes may be made and equivalents may be substituted for elements thereof without departing from the scope of the invention.

In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

Thus the scope of the invention should be determined by the appended claims and their legal equivalents, and not by the examples given.

That which is claimed is:

1. A method of compressing together first and second bone fragments using a bone compression device having:
   a fastener including:
   a shank portion with an externally-threaded portion and first and second ends,
   an enlarged head portion coupled to the first end of the shank portion, and
   a bore extending through the head and shank portions, and
   an anchor including:
   an internally-threaded bore, and
   first and second ends, with the first end being chamfer-shaped and the second end characterized by an enlarged shoulder;
   the method comprising:
   forming a first bore in the first bone fragment and at least partially through the second bone fragment;
   forming a second bore in the second bone fragment having a greater diameter than the first bore and positioned coaxial with the first bore, and defining a counterbore floor at an intersection of the first bore and the second bore;

inserting the chamfer-shaped first end of the anchor into the second bore;

positioning the anchor shoulder in contact with a rim of the second bore so as to define a small space between the counterbore floor of the second bore and the first end of the anchor, wherein the small space is characterized by a distance between three millimeters and a minimum distance required to prevent contact of the first end of the anchor with the counterbore floor of the second bore based on a bending moment of the second bone fragment;

inserting the shank portion of the fastener through the first bore and into the second bore; and advancing the externally-threaded portion of the fastener shank portion into the first end of the anchor until the fastener head portion contacts a rim of the first bore and the fastener and anchor operate to adjustably compress the first and second bone fragments together.

2. The method according to claim 1, wherein the bone compression device further comprises a lock characterized by an externally-threaded locking screw having a bore therethrough, and further comprising advancing the locking screw coaxially through the anchor towards the fastener and engaging the second end of the fastener shank portion to lock the relative positions of the fastener and the anchor.

3. The method according to claim 1, further comprising forming a countersunk depression in the first bone fragment about the rim of the first bore, wherein inserting the fastener through the first bore further comprises positioning the fastener head portion within the countersunk depression in the first bone fragment.

4. The method according to claim 1, further comprising forming a countersunk depression in the second bone fragment about the rim of the second bore, wherein inserting the anchor into the second bore further comprises positioning the anchor shoulder within the countersunk depression in the second bone fragment.

5. The method according to claim 1, further comprising squaring off the counterbore floor of the second bore.

6. The method according to claim 1, further comprising positioning at least one of a first washer about a perimeter of the anchor and in simultaneous contact with the anchor shoulder and the rim of the second bore, and a second washer about a perimeter of the fastener and in simultaneous contact with the fastener head portion and the rim of the first bore.

7. The method according to claim 6, further comprising selecting at least one of the first washer by shape and/or size to deliver compressive force about the first bone segment, and the second washer by shape and/or size to deliver compressive force about the second bone segment.

8. The method according to claim 1, further comprising selecting the fastener of the bone compression device from a plurality of fasteners ranging in length from 25 millimeters to 67 millimeters, such that the threaded portion of the fastener shank portion will be substantially received within the anchor when the fastener and the anchor compress the first and second bone fragments.

9. The method according to claim 1, wherein forming the second bore in the second bone fragment further comprises threading an internal surface portion of the second bore in the second bone fragment; and wherein inserting the first end of the anchor into the second bore further comprises threadedly receiving an externally-threaded portion of the anchor by the internal surface portion of the second bore.

\* \* \* \* \*